(12) United States Patent
Besidski et al.

(10) Patent No.: US 9,611,254 B2
(45) Date of Patent: Apr. 4, 2017

(54) TRIAZOLE COMPOUNDS AND THEIR USE AS GAMMA SECRETASE MODULATORS

(71) Applicant: Acturum Life Science AB, Sodertalje (SE)

(72) Inventors: Yevgeni Besidski, Tumba (SE); Ulrika Yngve, Uppsala (SE); Kim Paulsen, Huddinge (SE); Christian Erik Linde, Stockholm (SE); Gunnar Nordvall, Hagersten (SE); Istvan Macsari, Sodertalje (SE); Jonas Malmborg, Linkoping (SE)

(73) Assignee: Acturum Life Science AB, Sodertalje (SE)

( * ) Notice: Subject to any disclaimer, the term of this patent is extended or adjusted under 35 U.S.C. 154(b) by 0 days.

(21) Appl. No.: 14/895,512

(22) PCT Filed: Jun. 3, 2014

(86) PCT No.: PCT/EP2014/061498
§ 371 (c)(1),
(2) Date: Dec. 3, 2015

(87) PCT Pub. No.: WO2014/195321
PCT Pub. Date: Dec. 11, 2014

(65) Prior Publication Data
US 2016/0122326 A1    May 5, 2016

(30) Foreign Application Priority Data
Jun. 4, 2013 (SE) ...................... 1350683

(51) Int. Cl.
C07D 403/14 (2006.01)
A61K 31/4196 (2006.01)
A61K 45/06 (2006.01)

(52) U.S. Cl.
CPC ........ *C07D 403/14* (2013.01); *A61K 31/4196* (2013.01); *A61K 45/06* (2013.01)

(58) Field of Classification Search
None
See application file for complete search history.

(56) References Cited

U.S. PATENT DOCUMENTS

2010/0120874 A1    5/2010  Baumann et al.

FOREIGN PATENT DOCUMENTS

| WO | WO 2004/073705 | 9/2004 |
|---|---|---|
| WO | WO 2005/013985 | 2/2005 |
| WO | WO 2005/054193 | 6/2005 |
| WO | WO 2005/115990 | 12/2005 |
| WO | WO 2007/125364 | 11/2007 |
| WO | WO 2007/135969 | 11/2007 |
| WO | WO 2007/139149 | 12/2007 |
| WO | WO 2008/097538 | 8/2008 |
| WO | WO 2008/099210 | 8/2008 |
| WO | WO 2008/100412 | 8/2008 |
| WO | WO 2008/156580 | 12/2008 |
| WO | WO 2009/020580 | 2/2009 |
| WO | WO 2009/087127 | 7/2009 |
| WO | WO 2009/103652 | 8/2009 |
| WO | WO 2010/052199 | 5/2010 |
| WO | WO 2010/053438 | 5/2010 |
| WO | WO 2010/083141 | 7/2010 |
| WO | WO 2010/132015 | 11/2010 |
| WO | WO 2011/006903 | 1/2011 |
| WO | WO 2011/014535 | 2/2011 |
| WO | WO 2011/086098 | 7/2011 |
| WO | WO 2011/086099 | 7/2011 |
| WO | WO 2011/092272 | 8/2011 |
| WO | WO 2012/009309 | 1/2012 |

OTHER PUBLICATIONS

Beher D, Curr "Secrease Modulation and it's Promise for Alzheimer's Disease: a Rationale for Drug Discovery" *Top Med Chem*; 8(1):34-7; 2008.
Weggen et al. "A Subset of NSAIDs Lower Amyloidogenic AB42 Independently of Cyclooxygenase Activity" Nature 414(6860), 212-216 (2003).
Kounnas et al."*Modulation of Secretase Reduces B-Amyloid Deposition in a Transgenic Mouse Model of Alzheimer's Disease*" Neuron 67, 769-780 (2010).
Zettl et al."*Exploring the Chemical Space of γ-Secretase Modulators*" Trends Pharmacol. Sci. 31, 402-410 (2010).
Jarowicki, K.; et al. "Protecting Groups". Perkin Trans.1, issue 18, p. 2109, 2001.

*Primary Examiner* — Alicia L Otton
(74) *Attorney, Agent, or Firm* — Baker & Hostetler LLP

(57) ABSTRACT

The present invention relates to compounds of formula (I) and pharmaceutically acceptable salts thereof. The invention also relates to pharmaceutical compositions comprising these compounds, to processes for making these compounds, and to their use as medicaments for treatment and/or prevention of Aβ-related diseases.

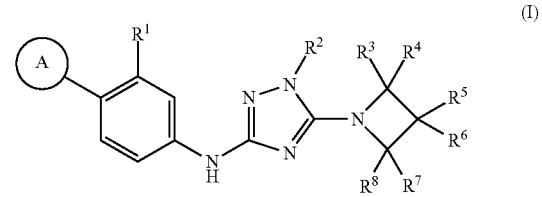

(I)

19 Claims, No Drawings

TRIAZOLE COMPOUNDS AND THEIR USE AS GAMMA SECRETASE MODULATORS

CROSS-REFERENCE TO RELATED APPLICATIONS

This application is the National Stage of International Application No. PCT/EP2014/061498, filed Jun. 3, 2014, which claims the benefit of SE application number 1350683-7, filed Jun. 4, 2013, the disclosures of which are incorporated herein by reference in their entireties.

The present invention relates to azetidinotriazole compounds and pharmaceutically acceptable salts thereof. The present invention also relates to pharmaceutical compositions comprising these compounds, to processes for making these compounds, and to their use as medicaments for the treatment and/or prevention of various Aβ-related diseases.

BACKGROUND

The prime neuropathological event distinguishing Alzheimer's disease (AD) is deposition of the amyloid β-peptide (Aβ) in brain parenchyma and cerebral vessels. A large body of genetic, biochemical and in vivo data support a pivotal role for Aβ in the pathological cascade that eventually leads to AD. Patients usually present early symptoms (commonly memory loss) in their sixth or seventh decades of life. The disease progresses with increasing dementia and elevated deposition of Aβ. In parallel, a hyperphosphorylated form of the microtubule-associated protein tau accumulates within neurons, leading to a plethora of deleterious effects on neuronal function. The prevailing working hypothesis regarding the temporal relationship between Aβ and tau pathologies states that Aβ deposition precedes tau aggregation in humans and animal models of the disease. Within this context, it is worth noting that the exact molecular nature of Aβ, mediating this pathological function is presently an issue under intense study. Most likely, there is a continuum of toxic species ranging from lower order Aβ oligomers to supramolecular assemblies such as Aβ fibrils.

The Aβ peptide is an integral fragment of the Type I protein APP (Aβ amyloid precursor protein), a protein ubiquitously expressed in human tissues. Aβ can be found in both plasma, cerebrospinal fluid (CSF) and in the medium from cultured cells, and is generated as a result of APP proteolysis. There are two main cleavages of APP that results in Aβ production, the so-called β-, and γ-cleavages. The β-cleavage, which generates the N terminus of Aβ, is catalyzed by the transmembrane aspartyl protease BACE1. The γ-cleavage, generating the Aβ C termini and subsequent release of the peptide, is affected by a multi-subunit aspartyl protease named γ-secretase. Both BACE1 and γ-secretase process APP at different sites, resulting in Aβ peptides of different lengths and heterologous N- and C-termini. The invention described herein covers all N-terminal variants of Aβ. Therefore, for the sake of simplicity, all N-terminal variants will be covered by the denotation Aβ.

The activity of γ-secretase causes the liberation of many Aβ peptides, such as Aβ37, Aβ38, Aβ39, Aβ40, Aβ42 and Aβ43, of which Aβ40 is the most common. These peptides show a different propensity to aggregate, and in particular Aβ42 is prone to form oligomers and fibrillar deposits. Intriguingly, human genetics strongly support a key role for Aβ42 as a key mediator of Alzheimer pathogenesis. Indeed, more than 150 different mutations causing familial Alzheimer's disease either result in an increase in the ratio of Aβ 42/40 peptides produced or affect the intrinsic aggregation behaviour of Aβ. Based on this knowledge, Aβ42 has become a prime target for therapeutic intervention in AD (Beher D, Curr Top Med Chem 2008; 8(1):34-7). Targeting Aβ42 at the level of γ-secretase activity must, however, be conducted with caution since γ-secretase catalyses proteolysis of many proteins, which have important physiological functions. Among its many substrates is the Notch receptor family, which signaling is essential for many different cell fate determination processes e.g. during embryogenesis and in the adult. As such, Aβ42 lowering strategies at the level of γ-secretase must be compatible with maintained Notch signaling.

It has been suggested that it is possible to combine γ-secretase interference and lowered Aβ42 production without obtaining toxic side effects due to impaired Notch signaling. There have, for instance, been reports which postulate that allosteric modulation of γ-secretase combines lowered Aβ42 production with maintained Notch signaling (Weggen et al. Nature 414(6860), 212-216 (2003); Kounnas et al. Neuron 67, 769-780 (2010); Zettl et al. Trends Pharmacol. Sci. 31, 402-410 (2010)). In addition, a number of compounds interfering with γ-secretase and Aβ production have been suggested in, e.g., WO2005/054193, WO2005/013985, WO2004/073705, WO2007/135969, WO2007/139149, WO2005/115990, WO2008/097538, WO2008/099210, WO2008/100412, WO2007/125364, WO2009/020580, WO2009/087127, WO2009/103652, WO2010/053438, WO2010/132015, WO2010/083141, WO2010/052199, WO2011/006903, WO2011/014535, WO2011/092272, WO2011/086098, WO2011/086099 and WO2012/009309.

The present invention relates to novel compounds, which inhibit the Aβ40 and Aβ42 production, increase Aβ37 and Aβ38 levels and maintain Notch signaling. These compounds are therefore useful in the prevention and/or treatment of, e.g. Alzheimer's Disease (AD). The compounds have preferably an improved pharmacokinetic and pharmacodynamic profile compared to known compounds, such as improved selectivity, an improved absorbtion after oral administration, improved first passage and faster onset of action, as well as reduced side effects, such as no or a minimized impairment on Notch signaling. Passage of the blood-brain barrier is preferably improved as well.

DISCLOSURE OF THE INVENTION

The present invention is directed to compounds according to formula (I)

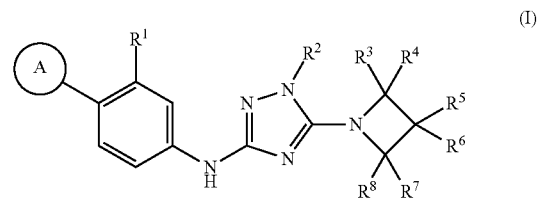

wherein:
A is 5- or 6-membered heteroaryl ring comprising at least one nitrogen atom, wherein the 5- or 6-membered heteroaryl ring is optionally substituted with one substituent selected from the group consisting of $C_{1-3}$-alkyl, $C_{1-3}$-alkoxy and halo;
$R^1$ is hydrogen, $C_{1-3}$-alkoxy, $C_{1-3}$-alkyl, cyano or halo;

$R^2$ is $C_{1-6}$-alkyl (optionally substituted with one or more substituents independently selected from the group consisting of hydroxy, halo and cyano), $C_{3-7}$-cycloalkyl-$C_{1-3}$-alkyl, heterocyclyl-$C_{1-3}$-alkyl or phenyl-$C_{1-3}$-alkyl (wherein any $C_{3-7}$-cycloalkyl, heterocyclyl and phenyl rings are optionally substituted with one or more substituents independently selected from the group consisting of fluoro and $C_{1-3}$-alkyl);

$R^3$, $R^5$ and $R^7$ are each independently selected from the group consisting of hydrogen, $C_{1-3}$-alkyl, $C_{3-7}$-cycloalkyl and phenyl, wherein $C_{1-3}$-alkyl, $C_{3-7}$-cycloalkyl and phenyl are optionally substituted with one or more substituents independently selected from the group consisting of fluoro and $C_{1-3}$-alkyl;

$R^4$, $R^6$ and $R^8$ are each independently selected from the group consisting of hydrogen, fluoro, $C_{1-3}$-alkyl and fluoro-$C_{1-3}$-alkyl;

or $R^3$ and $R^4$, or $R^5$ and $R^6$, or $R^7$ and $R^8$, together with the carbon atom to which they are attached, form a 3- to 7-membered saturated ring which optionally contains an oxygen or nitrogen atom, and which ring is optionally substituted with one or more substituents independently selected from the group consisting of fluoro and $C_{1-3}$-alkyl; as a free base or a pharmaceutically acceptable salt thereof.

It has surprisingly been found that these azetidinyl-substituents, especially azetidinyl substituent having an aromatic ring or a saturated cycloalkyl ring attached to it, show excellent pIC50 values. It is believed that the azetidinyl-group improved selectivity for Aβ42 and can be used to reduce the ratio Aβ 42/40 peptides. The compounds are expected to have improved blood-brain passage and thus an improved pharmacokinetic and dynamic profile, such as a faster onset of action and reduced side effects. This is especially true for the compounds, wherein $R^2$ is the more hydrophilic alcohol-substituent.

In one embodiment of the invention, A is a 5- or 6-membered heteroaryl ring selected from the group consisting of pyridinyl, pyridazinyl, pyrimidinyl, pyrazinyl, triazinyl, imidazolyl, thiazolyl, isothiazolyl, pyrryl, oxazolyl, isoxazolyl, pyrazolyl, triazolyl, tetrazolyl and thiadiazolyl, wherein the ring is optionally substituted with one $C_{1-3}$-alkyl substituent.

In another embodiment, A is selected from the group consisting of pyridinyl, pyridazinyl, pyrimidinyl, imidazolyl, thiazolyl, oxazolyl, pyrazolyl and triazolyl, and is substituted with one methyl substituent.

In yet another embodiment, A is imidazolyl substituted with methyl. In yet another embodiment, A is 4-methyl-1H-imidazol-1-yl.

In one embodiment, $R^1$ is hydrogen, methoxy or cyano. In another embodiment, $R^1$ is methoxy.

In one embodiment, $R^2$ is $C_{1-6}$-alkyl, which is optionally substituted with one or more substituents independently selected from the group consisting of hydroxy, halo and cyano.

In another embodiment, $R^2$ is $C_{1-4}$-alkyl, which is optionally substituted with one substituent independent selected from the group consisting of hydroxy, halo and cyano.

In another embodiment, $R^2$ is $C_{1-4}$-alkyl, which is optionally substituted with one hydroxy substituent. In yet another embodiment, $R^2$ is methyl or hydroxybutyl.

In one embodiment, $R^3$, $R^5$ and $R^7$ are each independently selected from the group consisting of hydrogen, $C_{1-3}$-alkyl and phenyl, wherein $C_{1-3}$-alkyl and phenyl are optionally substituted with one or more substituents independently selected from the group consisting of fluoro and $C_{1-3}$-alkyl.

In another embodiment, $R^3$, $R^5$ and $R^7$ are each independently hydrogen, $C_{1-3}$-alkyl or phenyl, wherein phenyl is optionally substituted with one or more substituents independently selected from the group consisting of fluoro and $C_{1-3}$-alkyl.

In another embodiment, $R^3$, $R^5$ and $R^7$ are each independently hydrogen, $C_{1-3}$-alkyl or phenyl.

In one embodiment, $R^4$, $R^6$ and $R^8$ are each independently hydrogen, fluoro or $C_{1-3}$-alkyl.

In one embodiment, $R^3$ and $R^4$, or $R^5$ and $R^6$, or $R^7$ and $R^8$, together with the carbon atom to which they are attached, form a 3- to 7-membered saturated ring, which is optionally substituted with one or more substituents independently selected from the group consisting of fluoro and $C_{1-3}$-alkyl;

In another embodiment, $R^3$ and $R^4$, or $R^5$ and $R^6$, or $R^7$ and $R^8$, together with the carbon atom to which they are attached, form a 4- to 6-membered saturated ring, which is optionally substituted with one or more substituents independently selected from the group consisting of $C_{1-3}$-alkyl and fluoro.

In yet another embodiment, $R^3$ and $R^4$, or $R^5$ and $R^6$, or $R^7$ and $R^8$, together with the carbon atom to which they are attached, form a cyclobutyl or cyclopentyl ring.

In one embodiment of the invention, A is selected from the group consisting of pyridinyl, pyridazinyl, pyrimidinyl, imidazolyl, thiazolyl, oxazolyl, pyrazolyl and triazolyl, and is substituted with one methyl substituent;

$R^1$ is hydrogen, methoxy or cyano;

$R^2$ is $C_{1-4}$-alkyl, which is optionally substituted with one substituent independent selected from the group consisting of hydroxy, halo and cyano;

$R^3$, $R^5$ and $R^7$ are each independently hydrogen, $C_{1-3}$-alkyl or phenyl, wherein phenyl is optionally substituted with one or more substituents independently selected from the group consisting of fluoro and $C_{1-3}$-alkyl;

$R^4$, $R^6$ and $R^8$ are each independently hydrogen, fluoro or $C_{1-3}$-alkyl;

or $R^3$ and $R^4$, or $R^5$ and $R^6$, or $R^7$ and $R^8$, together with the carbon atom to which they are attached, form a 4- to 6-membered saturated ring, which is optionally substituted with one or more substituents independently selected from the group consisting of $C_{1-3}$-alkyl and fluoro.

In another embodiment of the invention, A is selected from the group consisting of imidazolyl, thiazolyl, substituted with one methyl substituent;

$R^1$ is hydrogen or methoxy;

$R^2$ is $C_{1-4}$-alkyl, which is optionally substituted with one substituent independent selected from the group consisting of hydroxyl and halo;

$R^3$, $R^5$ and $R^7$ are each independently hydrogen, $C_{1-3}$-alkyl or phenyl;

$R^4$, $R^6$ and $R^8$ are each independently hydrogen, fluoro or $C_{1-3}$-alkyl;

or $R^3$ and $R^4$, or $R^5$ and $R^6$, or $R^7$ and $R^8$, together with the carbon atom to which they are attached, form a 4- to 6-membered saturated ring.

In another preferred embodiment of the invention, A is 4-methyl-1H-imidazol-1-yl and $R^1$ is methoxy.

In a further embodiment, the invention relates to compounds according to formula (Ia)

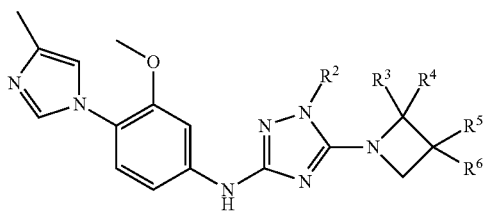

(Ia)

wherein:

$R^2$ is $C_{1-4}$-alkyl, which is substituted with one hydroxy substituent;

$R^3$ and $R^5$ are each independently hydrogen, $C_{1-3}$-alkyl or phenyl;

$R^4$ and $R^6$ are each independently hydrogen, fluoro or $C_{1-3}$-alkyl;

or $R^3$ and $R^4$, or $R^5$ and $R^6$, together with the carbon atom to which they are attached, form a cyclobutyl or cyclopentyl ring, which rings are optionally substituted with one or more substituents independently selected from the group consisting of $C_{1-3}$-alkyl and fluoro.

In another embodiment, the invention relates to a compound of formula (Ia), wherein:

$R^2$ is $C_{1-4}$-alkyl, which is substituted with one hydroxy substituent;

$R^3$ and $R^4$, or $R^5$ and $R^6$, together with the carbon atom to which they are attached, form a cyclobutyl or cyclopentyl ring, and the other of $R^3$, $R^4$, $R^5$ and $R^6$ are hydrogen.

Improved uptake in the gastrointestinal tract can be obtained by the addition of a more hydrophilic group, such as an alcohol group.

In yet another embodiment, the invention relates to a compound of formula (Ia), wherein:

$R^2$ is $C_{1-4}$-alkyl, which is optionally substituted with one hydroxy substituent;

$R^3$ is hydrogen and $R^5$ is phenyl, or $R^3$ is phenyl and $R^5$ is hydrogen; and $R^4$ and $R^6$ are each independently hydrogen or fluoro.

In a further embodiment, the invention relates to a compound of formula (Ia), wherein:

$R^2$ is $C_{1-4}$-alkyl, which is substituted with one hydroxy substituent;

$R^3$ is hydrogen and $R^5$ is phenyl, or $R^3$ is phenyl and $R^5$ is hydrogen; and $R^4$ and $R^6$ are each independently hydrogen or fluoro.

In another embodiment, the invention relates to a compound of formula (I), or a pharmaceutically acceptable salt thereof, selected from the group consisting of:

1-(3-(3-methoxy-4-(4-methyl-1H-imidazol-1-yl)phenylamino)-5-(3-phenylazetidin-1-yl)-1H-1,2,4-triazol-1-yl)-2-methylpropan-2-ol;

1-(5-(3-fluoro-3-phenylazetidin-1-yl)-3-(3-methoxy-4-(4-methyl-1H-imidazol-1-yl)phenylamino)-1H-1,2,4-triazol-1-yl)-2-methylpropan-2-ol;

N-(3-methoxy-4-(4-methyl-1H-imidazol-1-yl)phenyl)-1-methyl-5-(3-phenylazetidin-1-yl)-1H-1,2,4-triazol-3-amine;

N-(3-methoxy-4-(4-methyl-1H-imidazol-1-yl)phenyl)-1-methyl-5-(2-phenylazetidin-1-yl)-1H-1,2,4-triazol-3-amine;

1-(3-(3-methoxy-4-(4-methyl-1H-imidazol-1-yl)phenylamino)-5-(2-phenylazetidin-1-yl)-1H-1,2,4-triazol-1-yl)-2-methylpropan-2-ol;

1-(3-(3-methoxy-4-(4-methyl-1H-imidazol-1-yl)phenylamino)-5-(2-phenylazetidin-1-yl)-1H-1,2,4-triazol-1-yl)-2-methylpropan-2-ol, isomer 1;

1-(3-(3-methoxy-4-(4-methyl-1H-imidazol-1-yl)phenylamino)-5-(2-phenylazetidin-1-yl)-1H-1,2,4-triazol-1-yl)-2-methylpropan-2-ol, isomer 2;

1-(3-(3-methoxy-4-(4-methyl-1H-imidazol-1-yl)phenylamino)-5-(2-azaspiro[3.3]heptan-2-yl)-1H-1,2,4-triazol-1-yl)-2-methylpropan-2-ol; and 1-(3-(3-methoxy-4-(4-methyl-1H-imidazol-1-yl)phenylamino)-5-(1-azaspiro[3.4]octan-1-yl)-1H-1,2,4-triazol-1-yl)-2-methylpropan-2-ol.

In another embodiment, the invention relates to a compound of formula (I) (including compounds of formula (Ia)), or a pharmaceutically acceptable salt thereof, for use in therapy.

In another embodiment, the invention relates to a compound of formula (I), or a pharmaceutically acceptable salt thereof, for use in the treatment and/or prevention of an Aβ-related pathology.

In one embodiment, the invention relates to a compound of formula (I), or a pharmaceutically acceptable salt thereof, for use in the treatment and/or prevention of an Aβ-related pathology selected from the group consisting of Down's syndrome, a β-amyloid angiopathy, cerebral amyloid angiopathy, hereditary cerebral hemorrhage, a disorder associated with cognitive impairment, MCI ("mild cognitive impairment"), Alzheimer's disease, memory loss, attention deficit symptoms associated with Alzheimer's disease, neurodegeneration associated with Alzheimer's disease, dementia of mixed vascular origin, dementia of degenerative origin, pre-senile dementia, senile dementia, dementia associated with Parkinson's disease, progressive supranuclear palsy and cortical basal degeneration.

In another embodiment, the invention relates to a compound of formula (I), or a pharmaceutically acceptable salt thereof, for use in the treatment and/or prevention of Alzheimer's disease.

In another embodiment, the invention relates to the use of a compound of formula (I), or a pharmaceutically acceptable salt thereof, in the manufacture of a medicament for the treatment and/or prevention of an Aβ-related pathology.

In another embodiment, the invention relates to a method of treating and/or preventing an Aβ-related pathology in a mammal, comprising administering to said mammal a therapeutically effective amount of the compound of formula (I), or a pharmaceutically acceptable salt thereof.

In another embodiment, the invention relates to a pharmaceutical composition comprising a therapeutically effective amount of a compound of formula (I), or a pharmaceutically acceptable salt thereof, in association with a pharmaceutically acceptable excipient, carrier or diluent. In another embodiment, the invention relates to the pharmaceutical composition for use in therapy.

The treatment of Aβ-related pathology defined herein may be applied as a sole therapy or may involve, in addition to the compound of the invention, conjoint treatment with conventional therapy of value in treating one or more disease conditions referred to herein. Such conventional therapy may include one or more of the following categories of agents: acetyl cholinesterase inhibitors, anti-inflammatory agents, cognitive and/or memory enhancing agents, or atypical antipsychotic agents. Cognitive enhancing agents, memory enhancing agents and acetyl choline esterase inhibitors include onepezil (ARICEPT), galantamine (REMINYL or RAZADYNE), rivastigmine (EXELON), tacrine (COGNEX) and memantine (NAMENDA, AXURA or EBIXA). Atypical antipsychotic agents include Olanzapine (marketed as ZYPREXA), Aripiprazole (marketed as ABILIFY), Risperidone (marketed as RISPERDAL), Quetiapine (marketed as SEROQUEL), Clozapine (marketed as CLOZARIL), Ziprasidone (marketed as GEODON) and Olanzapine/Fluoxetine (marketed as SYMBYAX).

Such conjoint treatment may be achieved by way of the simultaneous, sequential or separate dosing of the individual components of the treatment. Such combination products employ the compounds, or pharmaceutically acceptable salts thereof, of the invention.

In one embodiment, the invention relates to a pharmaceutical composition comprising (i) a compound of formula (I), or a pharmaceutically acceptable salt thereof, (ii) an additional therapeutic agent, or a pharmaceutically acceptable salt thereof, and (iii) a pharmaceutically acceptable excipient, carrier or diluent.

In another embodiment, the invention relates to a pharmaceutical composition comprising (i) a compound of formula (I), or a pharmaceutically acceptable salt thereof, (ii) at least one agent selected from the group consisting of acetyl cholinesterase inhibitors, anti-inflammatory agents, cognitive enhancing agents, memory enhancing agents, and atypical antipsychotic agents, and (iii) a pharmaceutically acceptable excipient, carrier or diluent.

In another embodiment, the invention relates to a pharmaceutical composition comprising (i) a compound of formula (Ia), or a pharmaceutically acceptable salt thereof, (ii) at least one agent selected from the group consisting of onepezil (ARICEPT), galantamine (REMINYL or RAZADYNE), rivastigmine (EXELON), tacrine (COGNEX) and memantine (NAMENDA, AXURA or EBIXA). Atypical antipsychotic agents include Olanzapine (marketed as ZYPREXA), Aripiprazole (marketed as ABILIFY), Risperidone (marketed as RISPERDAL), Quetiapine (marketed as SEROQUEL), Clozapine (marketed as CLOZARIL), Ziprasidone (marketed as GEODON) and Olanzapine/Fluoxetine (marketed as SYMBYAX), and (iii) a pharmaceutically acceptable excipient, carrier or diluent.

Additional conventional chemotherapy or therapy may include one or more of the following categories of agents:
(i) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine and venlafaxine.
(ii) atypical antipsychotics such as quetiapine.
(iii) antipsychotics such as amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine and ziprasidone.
(iv) anxiolytics such as alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam and zolazepam.
(v) anticonvulsants such as carbamazepine, clonazepam, ethosuximide, felbamate, fosphenytoin, gabapentin, lacosamide, lamotrogine, levetiracetam, oxcarbazepine, phenobarbital, phenytoin, pregabaline, rufinamide, topiramate, valproate, vigabatrine and zonisamide.
(vi) Alzheimer's therapies such as donepezil, memantine, rivastigmine, galantamine and tacrine.
(vii) Parkinson's therapies such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase.
(viii) migraine therapies such as almotriptan, amantadine, bromocriptine, butalbital, cabergoline, dichloralphenazone, dihydroergotamine, eletriptan, frovatriptan, lisuride, naratriptan, pergolide, pizotiphen, pramipexole, rizatriptan, ropinirole, sumatriptan, zolmitriptan and zomitriptan.
(ix) stroke therapies such as abciximab, activase, NXY-059, citicoline, crobenetine, desmoteplase, repinotan, clopidogrel, eptifibatide, minocycline and traxoprodil.
(x) urinary incontinence therapies such as darafenacin, falvoxate, oxybutynin, propiverine, robalzotan, solifenacin and tolterodine.
(xi) neuropathic pain therapies including for example lidocain and capsaicin, and anticonvulsants such as gabapentin and pregabalin, and antidepressants such as duloxetine, venlafaxine, amitriptyline and klomipramine.
(xii) nociceptive pain therapies such as paracetamol; NSAIDS such as diclofenac, loxoprofen, naproxen, ketoprofen, ibuprofen, nabumeton, meloxicam and piroxicam; coxibs such as celecoxib, etoricoxib, lumiracoxib, rofecoxib, valdecoxib and parecoxib; and opioids such as morphine, oxycodone, buprenorfin and tramadol.
(xiii) insomnia therapies such as agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon and zolpidem.
(xiv) mood stabilizers such as carbamazepine, divalproex, gabapentin, lamotrigine, lithium, olanzapine, quetiapine, valproate, valproic acid and verapamil.

Such combination products employ the compounds of this invention within the dosage range described herein and the other pharmaceutically active compound or compounds within approved dosage ranges and/or the dosage described in the publication reference.

DEFINITIONS

The definitions set forth in this application are intended to clarify terms used throughout this application. The term "herein" means the entire application.

As used herein, the term "$C_{1-6}$-alkyl", used alone or as a suffix or prefix, is intended to include both branched and straight chain saturated aliphatic hydrocarbon groups having from 1 to 6 carbon atoms. Examples of $C_{1-6}$-alkyl include, but are not limited to, methyl, ethyl, n-propyl, i-propyl, n-butyl, i-butyl, sec-butyl, tert-butyl, pentyl and hexyl. Similarly, the term "$C_{1-3}$-alkyl" denotes alkyl having 1, 2 or 3 carbon atoms.

As used herein, the term "fluoro-$C_{1-3}$-alkyl", used alone or as a suffix or prefix, is intended to include both branched and straight chain saturated aliphatic hydrocarbon groups, having at least one fluoro substituent and having from 1 to 3 carbon atoms. Examples of fluoro-$C_{1-3}$-alkyl include, but are not limited to, fluoromethyl, difluoromethyl, trifluoromethyl, 1-fluoroethyl and 3-fluoropropyl.

As used herein, the term "$C_{1-3}$-alkoxy", used alone or as a suffix och prefix, refers to a $C_{1-3}$-alkyl radical which is attached to the remainder of the molecule through an oxygen atom. Examples of $C_{1-3}$-alkoxy include methoxy, ethoxy, n-propoxy and isopropoxy.

As used herein, "halo" or "halogen" refers to fluoro, chloro, bromo, and iodo.

As used herein, the term "heteroaryl" refers to a monocyclic heteroaromatic ring having 5 or 6 ring members and wherein at least one ring member is nitrogen. Examples include pyridinyl, pyridazinyl, pyrimidinyl, pyrazinyl, triazinyl, imidazolyl, thiazolyl, isothiazolyl, pyrryl, oxazolyl, isoxazolyl, pyrazolyl, triazolyl, tetrazolyl and thiadiazolyl.

As used herein, the term "$C_{3-7}$-cycloalkyl", used alone or as suffix or prefix, denotes a cyclic saturated alkyl group having a ring size from 3 to 7 carbon atoms and includes cyclopropyl, cyclobutyl, cyclopentyl, cyclohexyl and cycloheptyl.

As used herein, the term "$C_{3-7}$-cycloalkyl-$C_{1-3}$-alkyl" refers to a $C_{3-7}$-cycloalkyl group that is attached through a $C_{1-3}$-alkyl radical. Examples of $C_{3-7}$-cycloalkyl-$C_{1-3}$-alkyl include cyclopropylmethyl, 2-cyclopropylethyl and 2-cyclohexylethyl.

As used herein, the term "heterocyclyl" denotes a saturated monocyclic ring containing 3 to 7 ring atoms wherein 1 or 2 ring atoms are independently selected from nitrogen, sulphur and oxygen, and the remaining ring atoms are carbon. When present, the sulphur atom may be in an oxidized form (i.e., S=O or O=S=O). Examples of heterocyclyl include, but are not limited to, piperidinyl, piperazinyl, homopiperazinyl, azetidinyl, oxetanyl, morpholinyl, pyrrolidinyl, tetrahydropyranyl, tetrahydrofuranyl, tetrahydrothiopyranyl, tetrahydro-thiopyran 1-oxide and tetrahydro-thiopyran 1,1-dioxide.

As used herein, the term "heterocyclyl-$C_{1-3}$-alkyl" refers to a heterocyclyl group that is attached through a $C_{1-3}$-alkyl radical. Examples of heterocyclyl-$C_{1-3}$-alkyl include tetrahydropyran-4-ylmethyl, piperidin-4-ylmethyl, tetrahydrofuran-2-ylmethyl, oxetan-3-ylmethyl, 2-(4-morpholinyl) methyl and 2-(piperazin-1-yl)ethyl.

As used herein, the term "phenyl-$C_{1-3}$-alkyl" refers to a phenyl group that is attached through a $C_{1-3}$-alkyl radical. Examples of phenyl-$C_{1-3}$-alkyl include phenylmethyl (benzyl), 1-phenylethyl and 2-phenylethyl.

When $R^3$ and $R^4$, or $R^5$ and $R^6$, or $R^7$ and $R^8$, together with the carbon atom to which they are attached, form a 3- to 7-membered saturated ring which optionally contains an oxygen or nitrogen atom, this ring is a $C_{3-7}$-cycloalkyl ring, or is a heterocyclyl ring containing one oxygen or nitrogen atom.

As used herein, the term "optional" or "optionally" means that the subsequently described event or circumstance may but need not occur, and that the description includes instances where the event or circumstance occurs and instances where it does not.

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "protecting group" means temporary substituents protecting a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been extensively reviewed (see, e.g. Jarowicki, K.; Kocienski, P. Perkin Trans. 1, 2001, issue 18, p. 2109).

As used herein, "pharmaceutically acceptable salts" refer to forms of the disclosed compounds, wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like diethyl ether, ethyl acetate, ethanol, isopropanol, or acetonitrile are used.

A variety of compounds in the present invention may exist in particular geometric or stereoisomeric forms. The present invention takes into account all such compounds, including tautomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms, by synthesis from optically active starting materials, or synthesis using optically active reagents. When required, separation of the racemic material can be achieved by methods known in the art. All chiral, diastereomeric and racemic forms are intended, unless the specific stereochemistry or isomeric form is specifically indicated.

As used herein, "tautomer" means other structural isomers that exist in equilibrium resulting from the migration of a hydrogen atom. For example, keto-enol tautomerism occurs where the resulting compound has the properties of both a ketone and an unsaturated alcohol. Compounds and pharmaceutically acceptable salts of the invention further include hydrates and solvates thereof.

Compounds and salts described in this specification may be isotopically-labelled compounds (or "radio-labelled"). In that instance, one or more atoms are replaced by an atom having an atomic mass or mass number different from the atomic mass or mass number typically found in nature (i.e., naturally occurring). Examples of suitable isotopes that may be incorporated include $^2H$ (also written as "D" for deuterium), $^3H$ (also written as "T" for tritium), $^{11}C$, $^{13}C$, $^{14}C$, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I, and $^{131}$I. The radionuclide that is used will depend on the specific application of that radio-labelled derivative. For example, for in vitro receptor labelling and competition assays, compounds that incorporate $^{3}$H or $^{14}$C are often useful. For radio-imaging applications $^{11}$C or $^{18}$F are often useful. In some embodiments, the radionuclide is $^{3}$H. In some embodiments, the radionuclide is $^{14}$C. In some embodiments, the radionuclide is $^{11}$C. And in some embodiments, the radionuclide is $^{18}$F.

Compounds of the present invention may be administered orally, parenteral, buccal, vaginal, rectal, inhalation, insufflation, sublingually, intramuscularly, subcutaneously, topically, intranasally, intraperitoneally, intrathoracically, intravenously, epidurally, intrathecally, intracerebroventricularly and by injection into the joints.

The optimum dosage and frequency of administration will depend on the particular condition being treated and its severity; the age, sex, size and weight, diet, and general physical condition of the particular patient; other medication the patient may be taking; the route of administration; the formulation; and various other factors known to physicians and others skilled in the art.

The quantity of the compound to be administered will vary for the patient being treated and will vary from about 100 ng/kg of body weight to 100 mg/kg of body weight per day. For instance, dosages can be readily ascertained by those skilled in the art from this disclosure and the knowledge in the art. Thus, the skilled artisan can readily determine the amount of compound and optional additives, vehicles and/or carrier in compositions and to be administered in methods of the invention.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents; it can also be an encapsulating material.

Preparation of Compounds

The compounds of the present invention can be prepared as a free base or a pharmaceutically acceptable salt thereof by the processes described below. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Protective Groups in Organic Synthesis* by T. W. Greene, P. G. M Wutz, 3rd Edition, Wiley-Interscience, New York, 1999. Where necessary, the order of reaction process steps such as introduction of substituents can be altered.

Compounds of the present invention can be synthesized according to scheme 1.

Scheme 1. Syntheses of compound of formula (I).

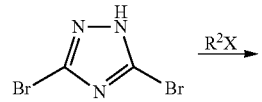

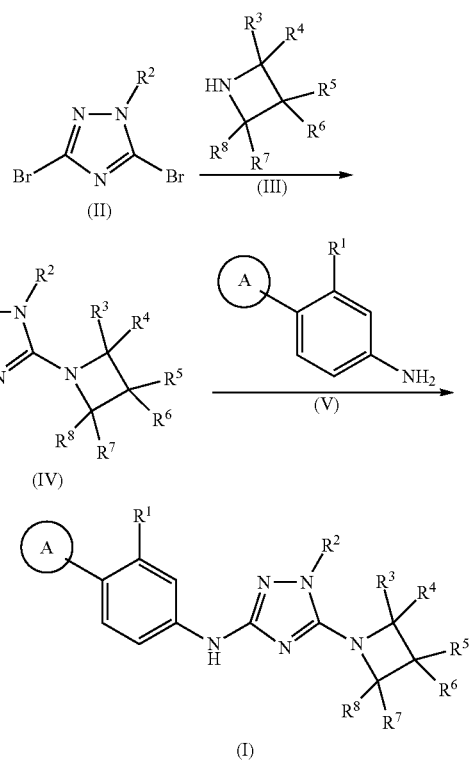

Dibromotriazole is reacted with an alkylating reagent of formula R$^2$X, where X is a leaving group such as chloro, bromo, iodo or sulfonyloxy, to give a compound of formula (II). The reaction is performed in the presence of a base such as a sodium alkoxide or sodium hydride at temperatures in the range of about +20° C. to +80° C. in a solvent such as DMF. Compound (II) is aminated with an azetidine of formula (III) to give a compound of formula (IV). The reaction is performed in the presence of a base such as potassium carbonate, diisopropylethylamine or triethylamine in a solvent such as dioxane or DMA, and at temperatures in the range of about +60° to +170° C. Compound (IV) is then reacted with a compound of formula (V) under Buchwald-Hartwig conditions to give a compound of formula (I). Examples of reagents used are palladium(II) acetate as catalyst, 9,9-dimethyl-4,5-bis(diphenylphosphino)xanthene as ligand, cesium carbonate as base, and dioxane and DMA or mixtures thereof as solvents. Said reaction can be performed at temperatures in the range of about 25° C. to 160° C.

Scheme 2. Synthesis of intermediate compounds of formula (V).

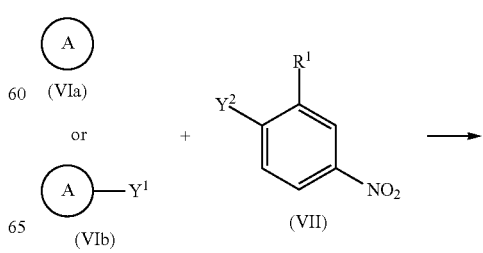

-continued

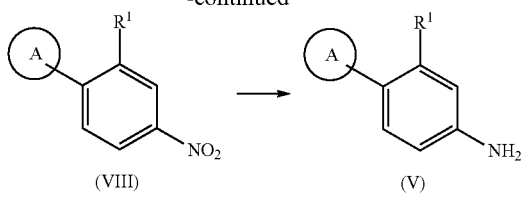

If ring A is attached to the phenyl ring through a nitrogen atom, a heteroaryl compound of formula (VIa) is reacted with a compound of formula (VII) wherein $Y^2$ is fluoro, chloro or bromo, to give a compound of formula (VIII). The reaction is performed in the presence of a base such as potassium carbonate or sodium hydroxide in a solvent such as acetonitrile, DMSO or DMF at temperatures in the range of about 20° C. and 150° C. Alternatively, the reaction can be catalysed by for example Cu(I)iodide.

If ring A is attached to the phenyl ring though a carbon atom, a heteroaryl compound of formula (VIb) wherein $Y^1$ is for example trialkylstannane, boronic acid or boronic ester, is reacted with a compound of formula (VII) wherein $Y^2$ is chlorine, bromine, iodine or triflate, to give a compound of formula (VIII). This reaction is performed under Stille or Suzuki conditions in the presence of for example a palladium catalyst, a ligand and a base.

Alternatively, the heterocyclic ring A can also be formed onto the phenyl ring. For example, a compound of formula (VII) wherein $Y^2$ is —C(O)CH$_2$Br can be transformed in several steps to form an appropriately substituted oxazole ring.

A compound of formula (VIII) can be transformed into a compound of formula (V) using standard conditions, for example catalytic hydrogenation with palladium on charcoal.

General Methods

NMR spectra were recorded on a 400 MHz or 500 MHz NMR spectrometer fitted with a probe of suitable configuration. Spectra were recorded at ambient temperature unless otherwise stated.

Chemical shifts are given in ppm down- and upfield from TMS (0.00 ppm). The following reference signals were used: TMS δ 0.00, or the residual solvent signal of DMSO-d$_6$ δ 2.50, CD$_3$OD δ 3.30, acetone-d$_6$ 2.04 or CDCl$_3$ δ 7.27 (unless otherwise indicated). Resonance multiplicities are denoted s, d, t, q, m, br and app for singlet, doublet, triplet, quartet, multiplet, broad and apparent, respectively.

Preparative or analytical High pressure liquid chromatography (HPLC) was performed on a reversed phase (RP) column. A linear gradient was applied using for example mobile phase A (0.1% Formic Acid in MilliQ H$_2$O or 0.1% NH$_3$ in MilliQ H$_2$O or 10 mM NH$_4$OAc and 5% CH$_3$CN in MilliQ H$_2$O) and B (CH$_3$OH or CH$_3$CN). Mass spectrometer (MS) analyses were performed in positive and/or negative ion mode using electrospray ionization (ESI+/−), atmospheric pressure photo ionization (APPI+/−) and/or atmospheric pressure chemical ionization (APCI+/−).

Gas chromatography (GC) was performed on a GC equipped with a mass spectrometer (MS) or a flame ionization detector (FID). The MS ion source was either an electron impact (EI) or a chemical ionization (CI, reactant gas methane).

Supercritical Fluid Chromatography (SFC) was performed on a straight phase column. An isocratic flow was applied using mobile phase A (CO$_2$) and for example mobile phase B (MeOH, EtOH or IPA optionally containing DEA).

The compounds have been named using CambridgeSoft MedChem ELN v2.1 or are according to IUPAC convention.

Abbreviations

DCM dichloromethane
DEA diethylamine
DMA dimethylacetamide
DMF dimethylformamide
EtOAc ethyl acetate
MeOH methanol
rt room temperature
TMS tetramethylsilane
t$_R$ retention time

EXAMPLES

The compounds described in this specification are further illustrated in the following Examples. These Examples are given by way of illustration only and are non-limiting.

Intermediate 1

3,5-Dibromo-1H-1,2,4-triazole

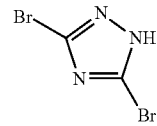

Solutions of bromine (6.1 mL, 119 mmol) in DCM (15 mL) and sodium hydroxide (6.78 g, 169 mmol) in water (20 mL) were simultaneously added dropwise to a stirred mixture of 1H-1,2,4-triazole (3.9 g, 56 mmol), water (50 mL) and DCM (15 mL) at 0° C. while keeping the reaction temperature below 20° C. The mixture was stirred at ambient temperature over night. Hydrochloric acid (conc, 2.0 mL, 66 mmol) was added. The solid was isolated by filtration, washed with water and dried in vacuum to yield the title compound as a solid (8.3 g, 65%).

MS (ESI$^−$) m/z 224 [M−H]$^−$.

Intermediate 2

3,5-Dibromo-1-(2-methylallyl)-1H-1,2,4-triazole

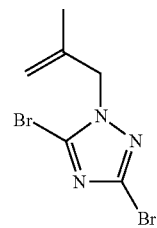

3,5-Dibromo-1H-1,2,4-triazole (1.5 g, 6.61 mmol) in DMF (13 mL) was treated with sodium tert-pentoxide (0.728 g, 6.61 mmol) and the mixture was stirred for 10 min at rt under nitrogen atmosphere. 3-Bromo-2-methylprop-1-ene (0.667 mL, 6.61 mmol) was added and the mixture was stirred at 40° C. for 2 hours. The mixture was poured onto water and extracted with diisopropylether (2×). The organic phase was washed with water (2×), brine and dried (sodium sulfate). The solvents were evaporated to give the title compound as a liquid (1.70 g, 91%).

GCMS (Cl) m/z 281 [M+]. $^1$H NMR (400 MHz, CDCl$_3$) δ ppm 1.74 (d, 3H) 4.69 (s, 2H) 4.81-4.86 (m, 1H) 5.05 (dd, 1H).

Intermediate 3

1-(3,5-Dibromo-1H-1,2,4-triazol-1-yl)-2-methylpropan-2-ol

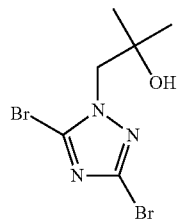

To a solution of mercuric acetate (1.827 g, 5.73 mmol) in water (15 mL), THF (15 mL) was added. The reaction flask was covered with Alumina foil. A solution of 3,5-dibromo-1-(2-methylallyl)-1H-1,2,4-triazole (0.895 g, 3.19 mmol) in THF (15 mL) was added under nitrogen atmosphere. The mixture was stirred at rt for 16 hours. Sodium borohydride (1.20 g, 31.9 mmol) was added in portions and the mixture was stirred for 1 hour. The mixture was diluted with water and extracted with EtOAc. The organic layer was washed with brine, dried over sodium sulfate) and concentrated to give the title compound as a liquid (0.91 g, 96%).

MS (ESI+) m/z 300 [M+H]+. $^1$H NMR (400 MHz, CDCl$_3$) δ ppm 1.28 (s, 6H) 4.15 (s, 2H).

Intermediate 4

3,5-Dibromo-1-methyl-1H-1,2,4-triazole

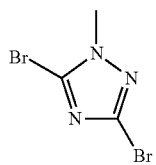

To a solution of 3,5-dibromo-1H-1,2,4-triazole (1.0 g, 4.41 mmol) in DMF (9 mL) sodium tert-pentoxide (0.485 g, 4.41 mmol) was added and the mixture was stirred for 10 min at rt under nitrogen atmosphere. Iodomethane (0.29 mL, 4.63 mmol) was added and the mixture was stirred at 40° C. for 2 hours. The mixture was poured onto water and extracted twice with diisopropylether. The organic phase was washed with water (2×), brine and dried over sodium sulfate. The solvents were evaporated to give the title compound as a solid (0.83 g, 78%).

MS (Cl) m/z 242 [M+]. $^1$H NMR (500 MHz, CDCl$_3$) δ ppm 3.89 (s, 3H).

Intermediate 5

1-(3-Bromo-5-(3-phenylazetidin-1-yl)-1H-1,2,4-triazol-1-yl)-2-methylpropan-2-ol

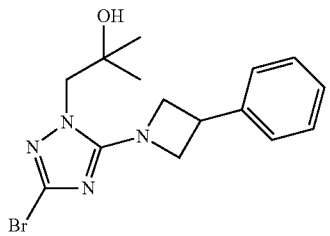 [SMILES: CC(C)(O)Cn1nc(Br)nc1N1CC(c2ccccc2)C1]

1-(3,5-Dibromo-1H-1,2,4-triazol-1-yl)-2-methylpropan-2-ol (1.0 g, 3.39 mmol) and 3-phenylazetidine (0.90 g, 6.77 mmol) were dissolved in a mixture of dioxane (15 mL) and DMA (1.5 mL). N,N-Diisopropylethylamine (1.18 mL, 6.77 mmol) was added and the reaction mixture was heated at 120° C. overnight. The solvents were evaporated and the residue was purified by column chromatography on silica gel eluting with a gradient of methanol in DCM yielding the title compound as a liquid (1150 mg, 97%).

MS (ESI−) m/z 349 [M−H]−. $^1$H NMR (500 MHz, CDCl$_3$) δ ppm 1.28 (s, 3H), 1.25 (s, 3H), 3.83 (s, 2H), 4.00 (quin, 1H), 4.26 (t, 2H), 4.58 (t, 2H), 7.28-7.32 (m, 1H), 7.33-7.41 (m, 4H).

Intermediate 6

1-(3-Bromo-5-(3-fluoro-3-phenylazetidin-1-yl)-1H-1,2,4-triazol-1-yl)-2-methylpropan-2-ol

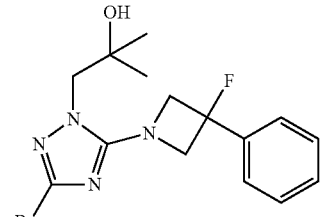

1-(3,5-Dibromo-1H-1,2,4-triazol-1-yl)-2-methylpropan-2-ol (121 mg, 0.40 mmol) and 3-fluoro-3-phenylazetidine hydrochloride (115 mg, 0.61 mmol) were dissolved in a mixture of dioxane (2 mL) and DMA (0.1 mL). N,N-Diisopropylethylamine (0.214 mL, 1.23 mmol) was added and the reaction mixture was heated at 120° C. for 72 h. The volatiles were evaporated and the residue was purified by column chromatography on silica gel eluting with a gradient of methanol in DCM yielding the title compound as a dry film (110 mg, 97%).

MS (ESI+) m/z 369 [M+H]+. $^1$H NMR (500 MHz, CDCl$_3$) δ ppm 1.27 (s, 6H), 3.84 (s, 2H), 4.54 (dd, 2H), 4.62-4.71 (m, 2H), 7.44-7.53 (m, 5H).

Intermediate 7

3-Bromo-1-methyl-5-(3-phenylazetidin-1-yl)-1H-1,2,4-triazole

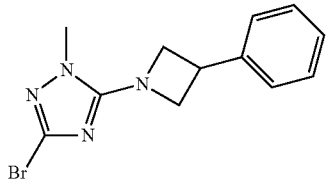 [SMILES: Cn1nc(Br)nc1N1CC(c2ccccc2)C1]

3,5-Dibromo-1-methyl-1H-1,2,4-triazole (128 mg, 0.53 mmol) and 3-phenylazetidine (127 mg, 0.96 mmol) were mixed in dioxane (2 mL). N,N-Diisopropylethylamine (0.232 mL, 1.33 mmol) was added. The mixture was stirred at 120° C. overnight. The solvents were removed and the residue was purified by silica column chromatography using a gradient of methanol in DCM giving the title compound as a liquid (58 mg, 37%).

MS (ESI$^+$) m/z 293 [M+H]$^+$. $^1$H NMR (500 MHz, CDCl$_3$) δ ppm 3.64 (s, 3H) 3.96-4.04 (m, 1H) 4.22 (t, 2H) 4.55 (t, 2H) 7.28-7.33 (m, 1H) 7.35-7.42 (m, 4H).

Intermediate 8

3-Bromo-1-methyl-5-(2-phenylazetidin-1-yl)-1H-1,2,4-triazole

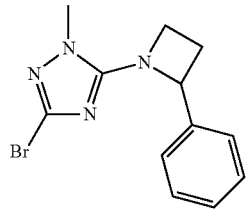 [SMILES: Cn1nc(Br)nc1N1CCC1c1ccccc1]

3,5-Dibromo-1-methyl-1H-1,2,4-triazole (200 mg, 0.83 mmol) and 2-phenylazetidine (177 mg, 1.33 mmol) were dissolved in DMF (5 mL). Potassium carbonate (344 mg, 2.49 mmol) was added. The mixture was heated at 170° C. for 2 hour in a microwave reactor. The mixture was cooled to rt, diluted with water and extracted with diisopropyl ether. The organic layer was washed with brine and dried over sodium sulfate. The solvents were removed to give the title compound as a liquid (225 mg, 92%).

MS (ESI$^+$) m/z 294 [M+H]$^+$. $^1$H NMR (400 MHz, CDCl$_3$) δ ppm 2.37-2.49 (m, 1H) 2.71-2.82 (m, 1H) 3.39 (s, 3H) 4.11-4.19 (m, 2H) 5.38 (t, 1H) 7.28-7.48 (m, 6H).

Intermediate 9

3-Bromo-1-(2-methylallyl)-5-(2-phenylazetidin-1-yl)-1H-1,2,4-triazole

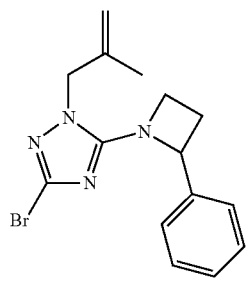 [SMILES: C=C(C)Cn1nc(Br)nc1N1CCC1c1ccccc1]

3,5-Dibromo-1-(2-methylallyl)-1H-1,2,4-triazole (500 mg, 1.78 mmol) and 2-phenylazetidine (379 mg, 2.85 mmol) were dissolved in DMF (13 mL). Potassium carbonate (738 mg, 5.34 mmol) was added. The mixture was heated at 170° C. for 2 hour in a microwave reactor. The mixture was diluted with water and extracted with diisopropyl ether. The organic layer was washed with brine, dried over sodium sulfate and concentrated to give the title compound as a liquid (593 mg, 100%).

MS (ESI$^+$) m/z 333 [M+H]$^+$. $^1$H NMR (400 MHz, DMSO-d$_6$) δ ppm 1.56 (s, 3H) 2.16-2.27 (m, 1H) 2.63-2.70 (m, 1H) 4.01-4.15 (m, 2H) 4.27-4.44 (m, 2H) 4.55 (s, 1H) 4.88-4.92 (m, 1H) 5.36 (t, 1H) 7.26-7.43 (m, 5H).

Intermediate 10

N-(3-Methoxy-4-(4-methyl-1H-imidazol-1-yl)phenyl)-1-(2-methylallyl)-5-(2-phenylazetidin-1-yl)-1H-1,2,4-triazol-3-amine

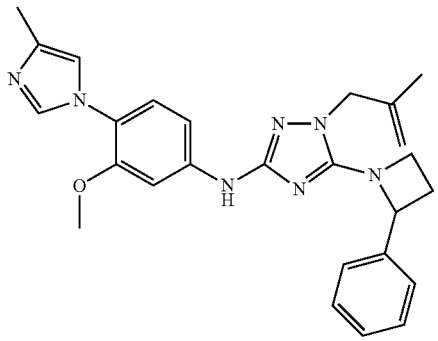 [SMILES: C=C(C)Cn1nc(Nc2ccc(-n3cnc(C)c3)c(OC)c2)nc1N1CCC1c1ccccc1]

3-Methoxy-4-(4-methyl-1H-imidazol-1-yl)aniline (0.362 g, 1.78 mmol), 3-bromo-1-(2-methylallyl)-5-(2-phenylazetidin-1-yl)-1H-1,2,4-triazole (0.593 g, 1.78 mmol), 9,9-dimethyl-4,5-bis(diphenylphosphino)xanthene (0.206 g, 0.36 mmol), palladium acetate (0.060 g, 0.27 mmol) and cesium carbonate (0.754 g, 2.31 mmol) in dioxane (10 mL) were placed in a vial under nitrogen atmosphere and the vial was sealed. The mixture was heated at 120° C. for 3.5 hours. The mixture was filtered and the filter was washed with DCM. The filtrate was concentrated and the residue was purified by column chromatography on silica using a gradient of methanol in dichloromethane. The solvents were removed in vacuum to give the title compound as a dry film (340 mg, 42%).

MS (ESI$^+$) m/z 456 [M+H]$^+$. $^1$H NMR (400 MHz, CDCl$_3$) δ ppm 1.62 (s, 3H) 2.29 (d, 3H) 2.32-2.44 (m 1H) 2.68-2.79 (m, 1H) 3.70 (s, 3H) 4.06-4.16 (m, 2H) 4.16-4.30 (m, 2H) 4.73 (s, 1H) 4.91-4.96 (m, 1H) 5.41 (t, 1H) 6.49 (s, 1H) 6.74 (dd, 1H) 6.82 (t, 1H) 7.06 (d, 1H) 7.29-7.33 (m, 1H) 7.35-7.41 (m, 2H) 7.42-7.47 (m, 3H) 7.59 (d, 1H).

Intermediate 11

1-(3-(3-Methoxy-4-(4-methyl-1H-imidazol-1-yl)phenylamino)-5-(2-phenylazetidin-1-yl)-1H-1,2,4-triazol-1-yl)propan-2-one

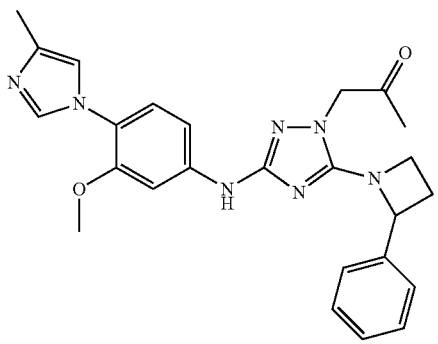 [SMILES: COc1cc(Nc2nc(N3CCC3c3ccccc3)n(CC(C)=O)n2)ccc1-n1cnc(C)c1]

Osmium tetroxide (2.5 wt % in tert-butanol, 0.16 mL, 0.010 mmol) was added to a mixture of N-(3-methoxy-4-(4-methyl-1H-imidazol-1-yl)phenyl)-1-(2-methylallyl)-5-(2-phenylazetidin-1-yl)-1H-1,2,4-triazol-3-amine (0.340 g, 0.75 mmol), sodium metaperiodate (0.639 g, 2.99 mmol) and 4-methylmorpholine N-oxide (0.111 g, 0.82 mmol) in acetonitrile (16 mL) and water (8 mL). The reaction mixture was stirred at rt for 16 hours under nitrogen atmosphere. The precipitate was removed by filtration and was washed with ethyl acetate. The filtrate was washed with sodium bicarbonate (sat, aq) and brine. The organic phase was dried over sodium sulfate and the volatiles were evaporated. The residue was purified by column chromatography on silica gel eluting with a gradient of methanol in DCM to give the title compound as a solid (165 mg, 48%).

MS (ESI$^+$) m/z 458 [M+H]$^+$. $^1$H NMR (500 MHz, CDCl$_3$) δ ppm 1.88 (s, 3H) 2.38 (br. s., 4H) 2.69-2.78 (m, 1H) 3.76 (s, 3H) 4.00-4.08 (m, 1H) 4.18-4.25 (m, 1H) 4.32 (s, 1H) 4.42 (s, 1H) 5.25-5.32 (m, 1H) 6.53-6.58 (m, 1H) 6.87 (br. s., 2H) 7.09 (d, 1H) 7.36 (s, 2H) 7.38-7.47 (m, 5H).

Intermediate 12

1-(3-Bromo-5-(2-azaspiro[3.3]heptan-2-yl)-1H-1,2,4-triazol-1-yl)-2-methylpropan-2-ol

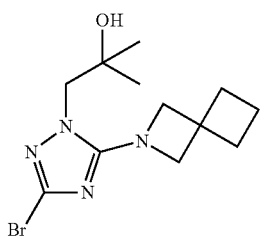 [SMILES: CC(C)(O)Cn1nc(Br)nc1N1CC2(CCC2)C1]

1-(3,5-Dibromo-1H-1,2,4-triazol-1-yl)-2-methylpropan-2-ol (121 mg, 0.40 mmol) and 2-azaspiro[3.3]heptane hydrochloride (108 mg, 0.81 mmol) were mixed in dioxane (2 mL) and DMA (0.1 mL). N,N-Diisopropylethylamine (0.282 mL, 1.62 mmol) was added and the mixture was heated at 120° C. overnight. The solvents were evaporated and the residue was purified by column chromatography on silica gel eluting with a gradient of methanol in DCM yielding the title compound as a dry film (100 mg, 78%).

MS (ESI$^+$) m/z 315 (M+H)$^+$. $^1$H NMR (500 MHz, CDCl$_3$) δ 1.22 (s, 3H), 1.28 (s, 3H), 1.67-1.78 (m, 1H), 1.78-2.00 (m, 3H), 2.22 (t, 2H), 3.50-3.71 (m, 1H), 3.77 (s, 1H), 3.97-4.20 (m, 3H).

Intermediate 13

1-(3-Bromo-5-(1-azaspiro[3.4]octan-1-yl)-1H-1,2,4-triazol-1-yl)-2-methylpropan-2-ol

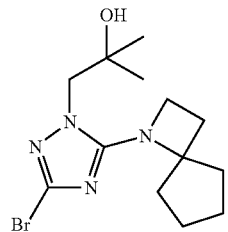 [SMILES: CC(C)(O)Cn1nc(Br)nc1N1CCC12CCCC2]

N,N-Diisopropylethylamine (0.315 mL, 1.81 mmol) was added to a solution of 1-(3,5-dibromo-1H-1,2,4-triazol-1-yl)-2-methylpropan-2-ol (135 mg, 0.45 mmol) and 1-azaspiro[3.4]octane (100 mg, 0.90 mmol) in dioxane (2 mL) and DMA (0.1 mL). The mixture was heated at 170° C. in a microwave reactor for 4 hours. (Mixture 1)

In parallel N,N-diisopropylethylamine (0.088 mL, 0.50 mmol) was added to a solution of 1-(3,5-dibromo-1H-1,2,4-triazol-1-yl)-2-methylpropan-2-ol (60 mg, 0.20 mmol) and 1-azaspiro[3.4]octane (26.8 mg, 0.24 mmol) in dioxane (1 mL). The mixture was stirred at 120° C. overnight. 1-Azaspiro[3.4]octane (27 mg, 0.24 mmol) was added and the mixture was heated in a microwave reactor at 140° C. for 22 hours. (Mixture 2).

Mixture 1 and mixture 2 were combined. The volatiles were removed in vacuum. The residue was dissolved in ethyl acetate and the solution was washed with water and brine. The organic layer was dried over sodium sulfate and concentrated. The residue was purified by silica column chromatography using a gradient of methanol in DCM to give the title compound as a dry film (106 mg, 50%).

MS (ESI$^+$) m/z 329 [M+H]$^+$. $^1$H NMR (500 MHz, CDCl$_3$) δ ppm 1.30 (s, 6H) 1.83-1.91 (m, 4H) 2.26 (t, 2H) 2.30 (td, 2H) 2.39 (t, 2H) 3.46-3.49 (m, 2H) 3.81 (s, 2H).

Example 1

1-(3-(3-Methoxy-4-(4-methyl-1H-imidazol-1-yl)phenylamino)-5-(3-phenylazetidin-1-yl)-1H-1,2,4-triazol-1-yl)-2-methylpropan-2-ol

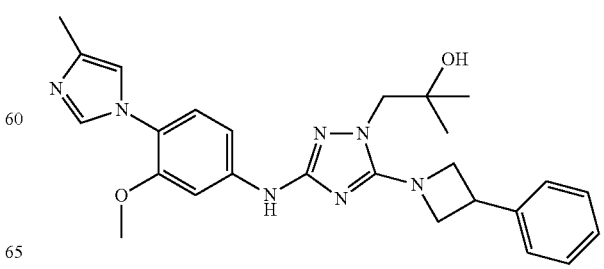

3-Methoxy-4-(4-methyl-1H-imidazol-1-yl)aniline (0.665 g, 3.27 mmol), 1-(3-bromo-5-(3-phenylazetidin-1-yl)-1H-1,2,4-triazol-1-yl)-2-methylpropan-2-ol (1.15 g, 3.27 mmol), 9,9-dimethyl-4,5-bis(diphenylphosphino)xanthene (0.379 g, 0.65 mmol), palladium acetate (0.110 g, 0.49 mmol), cesium carbonate (1.39 g, 4.26 mmol) and dioxane (17 mL) were mixed in a vial which was sealed under nitrogen atmosphere. The mixture was heated at 125° C. for 4 hours. Palladium acetate (50 mg) and 9,9-dimethyl-4,5-bis(diphenylphosphino)xanthene (100 mg) were added and the mixture was heated at 125° C. for 3 hours. The mixture was filtered through diatomeous earth, the filter plug was washed with methanol and DCM. The solvents were evaporated and the residue was purified by preparative chromatography to give the title compound as a solid (400 mg, 26%).

MS (ESI$^+$) m/z 474 [M+H]$^+$. $^1$H NMR (500 MHz, CDCl$_3$) δ ppm 1.26 (s, 6H) 2.30 (s, 3H) 3.78 (s, 2H) 3.84 (s, 3H) 3.97-4.05 (m, 1H) 4.21 (t, 2H) 4.47 (br. s., 1H) 4.50-4.56 (m, 2H) 6.65 (s, 1H) 6.76 (dd, 1H) 6.85 (s, 1H) 7.12 (d, 1H) 7.31 (td, 1H) 7.36-7.41 (m, 4H) 7.42 (d, 1H) 7.59 (s, 1H).

Example 2

1-(5-(3-Fluoro-3-phenylazetidin-1-yl)-3-(3-methoxy-4-(4-methyl-1H-imidazol-1-yl)phenylamino)-1H-1,2,4-triazol-1-yl)-2-methylpropan-2-ol

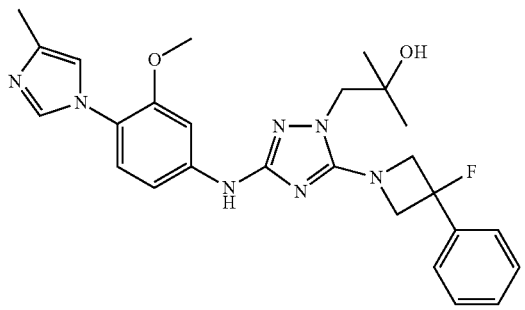 [SMILES: COc1cc(Nc2nc(N3CC(F)(c4ccccc4)C3)n(CC(C)(C)O)n2)ccc1-n1cnc(C)c1]

3-Methoxy-4-(4-methyl-1H-imidazol-1-yl)aniline (39 mg, 0.19 mmol), 1-(3-bromo-5-(3-fluoro-3-phenylazetidin-1-yl)-1H-1,2,4-triazol-1-yl)-2-methylpropan-2-ol (71 mg, 0.19 mmol), palladium acetate (9 mg, 0.04 mmol), 9,9-dimethyl-4,5-bis(diphenylphosphino)xanthene (17 mg, 0.03 mmol) and cesium carbonate (125 mg, 0.38 mmol) were mixed in dioxane (1 mL) and DMA (0.1 mL). The reaction mixture was heated at 120° C. under nitrogen atmosphere and overnight. The mixture was filtered through diatomeous earth and the filter plug was washed with methanol. The solvents were evaporated and the residue was purified by preparative chromatography yielding the title compound (13 mg, 14%).

MS (ESI$^+$) m/z 492 [M+H]$^+$. $^1$H NMR (500 MHz, CDCl$_3$) δ ppm 1.27 (s, 6H), 2.30 (s, 3H), 3.78 (s, 2H), 3.83 (s, 3H), 4.37 (s, 1H), 4.49 (dd, 9.30 Hz, 2H), 4.59-4.68 (m, 2H), 6.75-6.82 (m, 2H), 6.85 (s, 1H), 7.12 (d, 1H), 7.39-7.44 (m, 2H), 7.44-7.49 (m, 2H), 7.52-7.56 (m, 2H), 7.59 (s, 1H).

Example 3

N-(3-Methoxy-4-(4-methyl-1H-imidazol-1-yl)phenyl)-1-methyl-5-(3-phenylazetidin-1-yl)-1H-1,2,4-triazol-3-amine

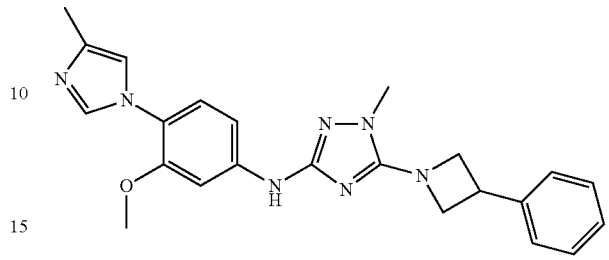

3-Methoxy-4-(4-methyl-1H-imidazol-1-yl)aniline (40 mg, 0.19 mmol), 3-bromo-1-methyl-5-(3-phenylazetidin-1-yl)-1H-1,2,4-triazole (57 mg, 0.19 mmol), palladium(II) acetate (7 mg, 0.03 mmol), 9,9-dimethyl-4,5-bis(diphenylphosphino)xanthene (22 mg, 0.04 mmol), cesium carbonate (82 mg, 0.25 mmol) and dioxane (2 mL) were mixed in a vial which was sealed under nitrogen atmosphere. The reaction mixture was heated at 120° C. for 3.5 hours. The mixture was filtered and the filter plug was washed with DCM. The solvents were evaporated and residue was purified by column chromatography on silica gel eluting with a gradient of methanol in DCM. followed by preparative HPLC to give the title compound as a solid (39 mg, 48%).

MS (ESI$^+$) m/z 416 [M+H]$^+$. $^1$H NMR (500 MHz, CDCl$_3$) δ ppm 2.37 (s, 3H) 3.61 (s, 3H) 3.86 (s, 3H) 4.01 (s, 1H) 4.21 (t, 2H) 4.54 (t, 2H) 6.52 (s, 1H) 6.86-6.92 (m, 2H) 7.13 (d, 1H) 7.29-7.33 (m, 1H) 7.39 (d, 4H) 7.43 (s, 1H) 7.76-7.84 (m, 1H).

Example 4

N-(3-Methoxy-4-(4-methyl-1H-imidazol-1-yl)phenyl)-1-methyl-5-(2-phenylazetidin-1-yl)-1H-1,2,4-triazol-3-amine

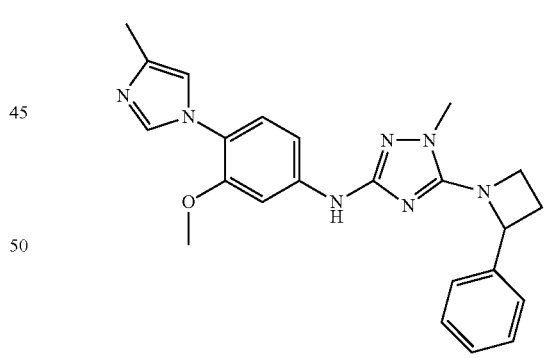

3-Methoxy-4-(4-methyl-1H-imidazol-1-yl)aniline (156 mg, 0.77 mmol), 3-bromo-1-methyl-5-(2-phenylazetidin-1-yl)-1H-1,2,4-triazole (225 mg, 0.77 mmol), palladium(II) acetate (26 mg, 0.12 mmol), 9,9-dimethyl-4,5-bis(diphenylphosphino)xanthene (89 mg, 0.15 mmol), cesium carbonate (325 mg, 1.00 mmol) and dioxane (5 mL) were mixed in a vial which was sealed under nitrogen atmosphere. The reaction mixture was heated at 120° C. in an oil-bath for 3.5 hours. The mixture was filtered and the filter was washed with DCM. The solvents were evaporated and residue was purified by column chromatography using a gradient of methanol in DCM, followed by preparative HPLC to give the title compound as a solid (144 mg, 45%).

MS (ESI⁺) m/z 416 [M+H]⁺. ¹H NMR (500 MHz, CDCl₃) δ ppm 7.60 (s, 1H) 7.47 (d, 2H) 7.36-7.41 (m, 3H) 7.28-7.33 (m, 1H) 7.08 (d, 1H) 6.83 (s, 1H) 6.79 (dd, 1H) 6.50 (s, 1H) 5.40 (t, 1H) 4.14-4.20 (m, 1H) 4.11 (q, 1H) 3.73 (s, 3H) 3.45 (s, 3H) 2.71-2.80 (m, 1H) 2.40-2.49 (m, 1H) 2.30 (s, 3H).

Example 5

1-(3-(3-Methoxy-4-(4-methyl-1H-imidazol-1-yl)phenylamino)-5-(2-phenylazetidin-1-yl)-1H-1,2,4-triazol-1-yl)-2-methylpropan-2-ol

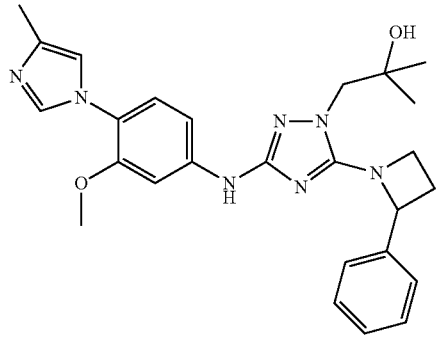 [SMILES: COc1cc(Nc2nc(N3CCC3c3ccccc3)n(CC(C)(C)O)n2)ccc1-n1cnc(C)c1]

Methylmagnesium bromide (2.06 mL, 2.89 mmol) was added to a suspension of lithium chloride (61 mg, 1.44 mmol) in THF (2 mL) and the mixture was kept under nitrogen atmosphere at 0° C. A solution of 1-(3-(3-methoxy-4-(4-methyl-1H-imidazol-1-yl)phenylamino)-5-(2-phenylazetidin-1-yl)-1H-1,2,4-triazol-1-yl)propan-2-one (165 mg, 0.36 mmol) in THF (1 mL) was added dropwise keeping the temperature at 0° C. The reaction was stirred at room temperature for 16 hours. The mixture was cooled to 0° C. and water was added followed by DCM. Ammonium chloride (aq, sat) was added to reach pH 7 and the phases were separated. The organic phase was dried over sodium sulfate and concentrated. The residue was purified by preparative HPLC to give the title compound as dry film (85 mg, 50%).

MS (ESI⁺) m/z 474 [M+H]⁺. ¹H NMR (500 MHz, CDCl₃) δ ppm 1.05 (s, 3H) 1.10 (s, 3H) 2.32 (s, 3H) 2.43 (dd, 1H) 2.73-2.82 (m, 1H) 3.62 (s, 2H) 3.75 (s, 3H) 4.12-4.18 (m, 2H) 4.45 (s, 1H) 5.39 (t, 1H) 6.57 (s, 1H) 6.70 (dd, 1H) 6.84 (s, 1H) 7.09 (d, 1H) 7.31-7.36 (m, 1H) 7.38-7.43 (m, 3H) 7.44-7.47 (m, 2H) 7.67 (br. s., 1H).

Example 6

1-(3-(3-Methoxy-4-(4-methyl-1H-imidazol-1-yl)phenylamino)-5-(2-phenylazetidin-1-yl)-1H-1,2,4-triazol-1-yl)-2-methylpropan-2-ol, isomer 1

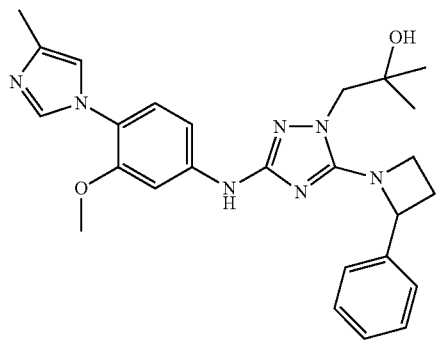 [SMILES: COc1cc(Nc2nc(N3CCC3c3ccccc3)n(CC(C)(C)O)n2)ccc1-n1cnc(C)c1]

Racemic 1-(3-(3-Methoxy-4-(4-methyl-1H-imidazol-1-yl)phenylamino)-5-(2-phenylazetidin-1-yl)-1H-1,2,4-triazol-1-yl)-2-methylpropan-2-ol (Example 5; 73 mg) was separated into its enantiomers by SFC chiral chromatography. The solvents were removed from the earliest eluted fractions to give the title compound as a dry film (26 mg, 36%).

MS (ESI⁺) m/z 474 [M+H]⁺. ¹H NMR (500 MHz, DMSO-d₆) δ ppm 1.19 (d, 6H) 2.11 (s, 3H) 2.16-2.26 (m, 1H) 2.65-2.74 (m, 1H) 3.65 (s, 3H) 3.68 (d, 2H) 4.04-4.13 (m, 1H) 4.15-4.25 (m, 1H) 4.76 (s, 1H) 5.41 (s, 1H) 6.88-6.93 (m, 1H) 6.95 (s, 1H) 7.09 (d, 1H) 7.26 (s, 1H) 7.33-7.38 (m, 2H) 7.39-7.44 (m, 2H) 7.57 (s, 1H) 7.62 (d, 1H) 9.21 (s, 1H).

Chiral SFC: Column LuxC2; 4.6*250 mm; 5um; mobile phase 40% MeOH+0.1% DEA; 60% CO₂; Flow 3 mL/min; t_R: 7.36 min.

Example 7

1-(3-(3-Methoxy-4-(4-methyl-1H-imidazol-1-yl)phenylamino)-5-(2-phenylazetidin-1-yl)-1H-1,2,4-triazol-1-yl)-2-methylpropan-2-ol, isomer 2

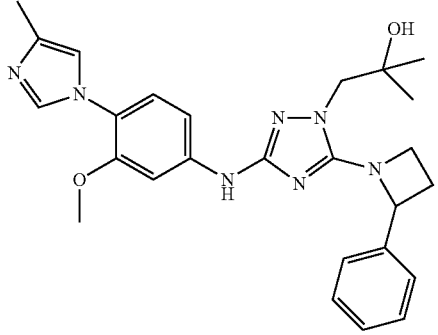 [SMILES: COc1cc(Nc2nc(N3CCC3c3ccccc3)n(CC(C)(C)O)n2)ccc1-n1cnc(C)c1]

Racemic 1-(3-(3-Methoxy-4-(4-methyl-1H-imidazol-1-yl)phenylamino)-5-(2-phenylazetidin-1-yl)-1H-1,2,4-triazol-1-yl)-2-methylpropan-2-ol (Example 5; 73 mg) was separated by SFC chiral chromatography. Fractions containing latest eluted enantiomer were collected and concentrated to give the title compound as a dry film (35 mg, 48%).

MS (ESI⁺) m/z 474 [M+H]⁺. ¹H NMR (500 MHz, DMSO-d₆) δ ppm 1.19 (d, 6H) 2.11 (s, 3H) 2.16-2.26 (m, 1H) 2.65-2.73 (m, 1H) 3.65 (s, 3H) 3.68 (d, 2H) 4.04-4.12 (m, 1H) 4.16-4.23 (m, 1H) 4.77 (s, 1H) 5.41 (s, 1H) 6.87-6.92 (m, 1H) 6.95 (s, 1H) 7.09 (d, 1H) 7.26 (s, 1H) 7.33-7.39 (m, 2H) 7.39-7.44 (m, 2H) 7.57 (s, 1H) 7.62 (d, 1H) 9.22 (s, 1H).

Chiral SFC: Column LuxC2; 4.6*250 mm; 5 μm; mobile phase 40% MeOH+0.1% DEA; 60% CO₂; Flow 3 mL/min; t_R: 10.12 min.

Example 8

1-(3-(3-Methoxy-4-(4-methyl-1H-imidazol-1-yl)phenylamino)-5-(2-azaspiro[3.3]heptan-2-yl)-1H-1,2,4-triazol-1-yl)-2-methylpropan-2-ol

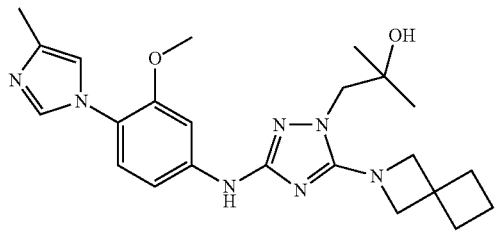 [SMILES: COc1cc(Nc2nc(N3CC4(CCC4)C3)n(CC(C)(C)O)n2)ccc1-n1cnc(C)c1]

3-Methoxy-4-(4-methyl-1H-imidazol-1-yl)aniline (64 mg, 0.32 mmol), 1-(3-bromo-5-(2-azaspiro[3.3]heptan-2-yl)-1H-1,2,4-triazol-1-yl)-2-methylpropan-2-ol (100 mg, 0.32 mmol), palladium acetate (14 mg, 0.06 mmol), 9,9-dimethyl-4,5-bis(diphenylphosphino)xanthene (28 mg, 0.05 mmol) and cesium carbonate (206 mg, 0.63 mmol) were mixed in dioxane (2 mL) and DMA (0.1 mL) under nitrogen atmosphere. The mixture was heated at 120° C. overnight. The reaction mixture was filtered through diatomeous earth and the filter plug was washed with methanol. The filtrate was concentrated and the residue was purified by preparative chromatography to give the title compound as a solid (27 mg, 20%).

MS (ESI$^+$) m/z 438 [M+H]$^+$. $^1$H NMR (500 MHz, CDCl$_3$) δ 1.23 (s, 6H), 1.86 (quin, 2H), 2.22 (t, 4H), 2.29 (s, 3H), 3.73 (s, 2H), 3.82 (s, 3H), 4.09 (s, 4H), 4.59 (br. s., 1H), 6.73 (dd, 2.05 Hz, 1H), 6.83 (s, 1H), 7.09 (d, 1H), 7.39 (d, 1H), 7.58 (s, 1H).

Example 9

1-(3-(3-Methoxy-4-(4-methyl-1H-imidazol-1-yl)phenylamino)-5-(1-azaspiro[3.4]octan-1-yl)-1H-1,2,4-triazol-1-yl)-2-methylpropan-2-ol

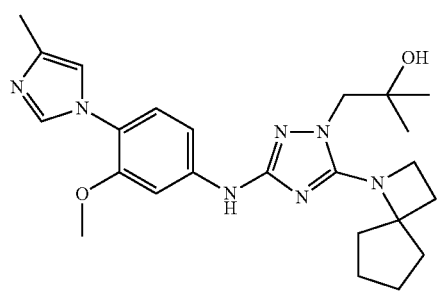 [SMILES: COc1cc(Nc2nc(N3CCC34CCCC4)n(CC(C)(C)O)n2)ccc1-n1cnc(C)c1]

3-Methoxy-4-(4-methyl-1H-imidazol-1-yl)aniline (62 mg, 0.30 mmol), 1-(3-bromo-5-(1-azaspiro[3.4]octan-1-yl)-1H-1,2,4-triazol-1-yl)-2-methylpropan-2-ol (100 mg, 0.30 mmol), 9,9-dimethyl-4,5-bis(diphenylphosphino)xanthene (35 mg, 0.06 mmol), palladium acetate (10 mg, 0.05 mmol), cesium carbonate (129 mg, 0.39 mmol) and dioxane (3 mL) were mixed in a vial which was sealed under nitrogen atmosphere. The mixture was heated at 120° C. for 3 hours. The mixture was diluted with water and extracted with ethyl acetate. The organic phase was dried over sodium sulfate and concentrated. The residue was purified by preparative HPLC to give the title compound as a dry film (12 mg, 9%).

MS (ESI$^+$) m/z 452 [M+H]$^+$. $^1$H NMR (500 MHz, CDCl$_3$) δ ppm 1.28-1.33 (m, 6H) 1.86 (quin, 2H) 2.22-2.34 (m, 6H) 2.41 (t, 2H) 3.42-3.50 (m, 4H) 3.75 (s, 2H) 3.81 (s, 3H) 5.03 (t, 1H) 5.44 (br. s., 1H) 6.68 (s, 1H) 6.79 (dd, 1H) 6.83 (s, 1H) 7.08 (d, 1H) 7.46 (d, 1H) 7.55 (s, 1H).

Biological Assays

The level of activity of the compounds on Aβ formation was tested using the following methods:

HEK Assay

Compounds were diluted in 100% DMSO and stored at 20° C. prior to use. Human Embryonic Kidney (HEK) cell line stably expressing APP with the Swedish mutation (APPswe) was cultured using Dulbecco's Modified Eagles medium (DMEM) supplied with 4500 g/L glucose, Na-pyruvate and GlutaMAX, 10% Foetal bovine serum, 100 U/mL penicillin-streptomycin (PEST), 1× non-essential amino acids (NEAA), 10 μM Hepes, 100 μg/mL Zeocine. Cells at about 80% confluence were washed with PBS, detached from culture flasks using 1× Trypsin/EDTA diluted in PBS, re-suspended in cell media and plated in 384-well poly-d-lysine coated cell culture plates at about 10000-15000 cells/well, in 25 μL cell media. Optionally, cryo-preserved cells (frozen and stored at −140° C. in 90% cell media and 10% DMSO) were thawed, washed and plated as above. Next the cells were incubated for 15-24 h at 37° C. and 5% CO$_2$, after which cell medium was changed. Fresh medium containing test compound diluted ×200 from pre-pared compound plate was added to the cells before further incubation for 4-6 hours at 37° C. and 5% CO$_2$. After incubation with test compound the amount of Aβ peptides, including Aβ42, Aβ40, Aβ39, Aβ38 and Aβ37, secreted to cell medium was analyzed using the electrochemilumines-cence assay technology from Meso Scale Discovery Technology, in combination with specific antibodies raised against the different Aβ peptides. Potential cytotoxic effects of the compounds were assayed by measuring the ATP content (ViaLight) from cell lysate.

PCN Assay

Compounds were diluted in 100% DMSO and stored at 20° C. prior to use. Primary cortical neuronal cells (PCN) were isolated from 16-day mouse embryos and cultured in Ham's F12 media containing 10% Foetal bovine serum, 10 mM Hepes, 2 mM L-glutamine and 100 U/mL Penicillin-Streptomycin. 150000-250000 cells/well, in 200 μL cell media were seeded onto 96-well poly-D-Lysine coated plates. After incubation at 37° C., 5% CO$_2$ for five days, the media was exchanged for fresh medium containing test compound diluted ×100, before further incubation for 16-20 hours at 37° C. and 5% CO$_2$. After incubation with test compound the amount of Aβ42 peptides secreted to cell medium was analyzed using the solid phase sandwich Enzyme-Linked-Immuno-Sorbent Assay (ELISA)-kit from Invitrogen for detection of mouse βAmyloid 1-42. Potential cytotoxic effects of the compounds were assayed by measuring the ATP content (Via Light) from cell lysate.

Results

Biological data on exemplified compounds are given below in Table 1.

TABLE 1

| pIC$_{50}$ values in the HEK and PCN assays for the examples of the present invention. | | |
|---|---|---|
| Example number | pIC50 Aβ42 HEK assay | pIC50 Aβ42 PCN assay |
| 1 | 7.4 | 7.8 |
| 2 | 7.3 | 7.5 |
| 3 | 7.4 | 7.1 |
| 4 | 7.6 | 7.6 |
| 5 | 7.6 | 7.5 |
| 6 | 7.6 | 7.2 |
| 7 | 7.8 | 7.7 |
| 8 | 7.3 | 7.2 |
| 9 | 7.5 | 7.5 |

The total IC50 Aβ and the ratio of Aβ 42/40 was improved.

The invention claimed is:

1. A compound of formula (I)

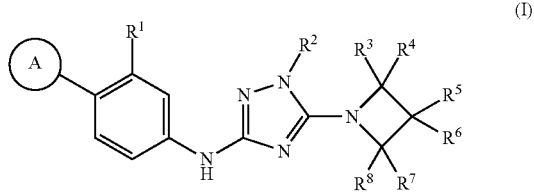

wherein:
A is 5- or 6-membered heteroaryl ring comprising at least one nitrogen atom, wherein the 5- or 6-membered heteroaryl ring is optionally substituted with one substituent selected from the group consisting of $C_{1-3}$-alkyl, $C_{1-3}$-alkoxy and halo;
$R^1$ is hydrogen, $C_{1-3}$-alkoxy, $C_{1-3}$-alkyl, cyano or halo;
$R^2$ is $C_{1-6}$-alkyl optionally substituted with one or more substituents independently selected from the group consisting of hydroxy, halo and cyano; $C_{3-7}$-cycloalkyl-$C_{1-3}$-alkyl; heterocyclyl-$C_{1-3}$-alkyl; or phenyl-$C_{1-3}$-alkyl; wherein any $C_{3-7}$-cycloalkyl, heterocyclyl, and phenyl rings are optionally substituted with one or more substituents independently selected from the group consisting of fluoro and $C_{1-3}$-alkyl;
$R^3$, $R^5$ and $R^7$ are each independently selected from the group consisting of hydrogen, $C_{1-3}$-alkyl, $C_{3-7}$-cycloalkyl and phenyl, wherein the $C_{1-3}$-alkyl, $C_{3-7}$-cycloalkyl, and phenyl are optionally substituted with one or more substituents independently selected from the group consisting of fluoro and $C_{1-3}$-alkyl;
$R^4$, $R^6$ and $R^8$ are each independently hydrogen, fluoro, $C_{1-3}$-alkyl, or fluoro-$C_{1-3}$-alkyl;
or $R^3$ and $R^4$, or $R^5$ and $R^6$, or $R^7$ and $R^8$, together with the carbon atom to which they are attached, form a 3- to 7-membered saturated ring which optionally contains an oxygen or nitrogen atom, and which ring is optionally substituted with one or more substituents independently selected from the group consisting of fluoro and $C_{1-3}$-alkyl;
or a pharmaceutically acceptable salt thereof.

2. The compound according to claim 1, or a pharmaceutically acceptable salt thereof, wherein A is a 5- or 6-membered heteroaryl ring selected from the group consisting of pyridinyl, pyridazinyl, pyrimidinyl, pyrazinyl, triazinyl, imidazolyl, thiazolyl, isothiazolyl, pyrryl, oxazolyl, isoxazolyl, pyrazolyl, triazolyl, tetrazolyl and thiadiazolyl, wherein the ring is optionally substituted with one $C_{1-3}$-alkyl substituent.

3. The compound according to claim 1, or a pharmaceutically acceptable salt thereof, wherein $R^2$ is $C_{1-6}$-alkyl, which is optionally substituted with one or more substituents independently selected from the group consisting of hydroxy, halo and cyano.

4. The compound according to claim 1, or a pharmaceutically acceptable salt thereof, wherein $R^3$, $R^5$ and $R^7$ are each independently selected from the group consisting of hydrogen, $C_{1-3}$-alkyl and phenyl, wherein $C_{1-3}$-alkyl and phenyl are optionally substituted with one or more substituents independently selected from the group consisting of fluoro and $C_{1-3}$-alkyl.

5. The compound according to claim 1, or a pharmaceutically acceptable salt thereof, wherein $R^4$, $R^6$ and $R^8$ are each independently hydrogen, fluoro or $C_{1-3}$-alkyl.

6. The compound according to claim 1, or a pharmaceutically acceptable salt thereof, wherein $R^3$ and $R^4$, or $R^5$ and $R^6$, or $R^7$ and $R^8$, together with the carbon atom to which they are attached, form a 4- to 6-membered saturated ring, which is optionally substituted with one or more substituents independently selected from the group consisting of $C_{1-3}$-alkyl and fluoro.

7. The compound according to claim 1, or a pharmaceutically acceptable salt thereof, wherein A is 4-methyl-1H-imidazol-1-yl and $R^1$ is methoxy.

8. The compound according to claim 1, or a pharmaceutically acceptable salt thereof, having formula (Ia)

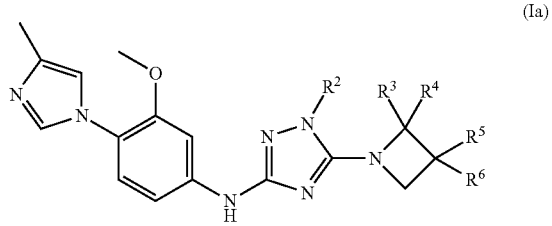

wherein:
$R^2$ is $C_{1-4}$-alkyl, which is optionally substituted with one hydroxy substituent;
$R^3$ and $R^5$ are each independently hydrogen, $C_{1-3}$-alkyl or phenyl;
$R^4$ and $R^6$ are each independently hydrogen, fluoro or $C_{1-3}$-alkyl;
or $R^3$ and $R^4$, or $R^5$ and $R^6$, together with the carbon atom to which they are attached, form a cyclobutyl or cyclopentyl ring, which rings are optionally substituted with one or more substituents independently selected from the group consisting of $C_{1-3}$-alkyl and fluoro.

9. The compound according to claim 8, or a pharmaceutically acceptable salt thereof, wherein:
$R^2$ is $C_{1-4}$-alkyl, which is optionally substituted with one hydroxy substituent;
$R^3$ and $R^5$ are each independently hydrogen or phenyl;
$R^4$ and $R^6$ are each independently hydrogen or fluoro;
or $R^3$ and $R^4$, or $R^5$ and $R^6$, together with the carbon atom to which they are attached, form a cyclobutyl or cyclopentyl ring.

10. The compound according to claim 8, or a pharmaceutically acceptable salt thereof, wherein:
$R^2$ is $C_{1-4}$-alkyl, which is optionally substituted with one hydroxy substituent;

R³ is hydrogen and R⁵ is phenyl, or R³ is phenyl and R⁵ is hydrogen; and

R⁴ and R⁶ are each independently hydrogen or fluoro.

11. The compound according to claim 1, selected from the group consisting of:
- 1-(3-(3-methoxy-4-(4-methyl-1H-imidazol-1-yl)phenylamino)-5-(3-phenylazetidin-1-yl)-1H-1,2,4-triazol-1-yl)-2-methylpropan-2-ol;
- 1-(5-(3-fluoro-3-phenylazetidin-1-yl)-3-(3-methoxy-4-(4-methyl-1H-imidazol-1-yl)phenylamino)-1H-1,2,4-triazol-1-yl)-2-methylpropan-2-ol;
- N-(3-methoxy-4-(4-methyl-1H-imidazol-1-yl)phenyl)-1-methyl-5-(3-phenylazetidin-1-yl)-1H-1,2,4-triazol-3-amine;
- N-(3-methoxy-4-(4-methyl-1H-imidazol-1-yl)phenyl)-1-methyl-5-(2-phenylazetidin-1-yl)-1H-1,2,4-triazol-3-amine;
- 1-(3-(3-methoxy-4-(4-methyl-1H-imidazol-1-yl)phenylamino)-5-(2-phenylazetidin-1-yl)-1H-1,2,4-triazol-1-yl)-2-methylpropan-2-ol;
- 1-(3-(3-methoxy-4-(4-methyl-1H-imidazol-1-yl)phenylamino)-5-(2-phenylazetidin-1-yl)-1H-1,2,4-triazol-1-yl)-2-methylpropan-2-ol, isomer 1;
- 1-(3-(3-methoxy-4-(4-methyl-1H-imidazol-1-yl)phenylamino)-5-(2-phenylazetidin-1-yl)-1H-1,2,4-triazol-1-yl)-2-methylpropan-2-ol, isomer 2;
- 1-(3-(3-methoxy-4-(4-methyl-1H-imidazol-1-yl)phenylamino)-5-(2-azaspiro[3.3]heptan-2-yl)-1H-1,2,4-triazol-1-yl)-2-methylpropan-2-ol; and
- 1-(3-(3-methoxy-4-(4-methyl-1H-imidazol-1-yl)phenylamino)-5-(1-azaspiro[3.4]octan-1-yl)-1H-1,2,4-triazol-1-yl)-2-methylpropan-2-ol;
- or a pharmaceutically acceptable salt of any foregoing compound.

12. A pharmaceutical composition comprising as active ingredient a therapeutically effective amount of a compound according to claim 1, or a pharmaceutically acceptable salt thereof, in association with a pharmaceutically acceptable excipient, carrier or diluent.

13. A pharmaceutical composition comprising
- (i) a compound of formula (I) according to claim 1, or a pharmaceutically acceptable salt thereof,
- (ii) an additional therapeutic agent, or a pharmaceutically acceptable salt thereof, and
- (iii) a pharmaceutically acceptable excipient, carrier or diluent.

14. The pharmaceutical composition according to claim 13, wherein the additional therapeutic agent is selected from the group consisting of acetyl cholinesterase inhibitors, anti-inflammatory agents, cognitive enhancing agents, memory enhancing agents, and atypical antipsychotic agents.

15. A pharmaceutical composition comprising
- (i) a compound of formula (Ia) according to claim 8, or a pharmaceutically acceptable salt thereof,
- (ii) at least one agent selected from the group consisting of onepezil, galantamine, rivastigmine, tacrine and memantine, Olanzapine, Aripiprazole, Risperidone, Quetiapine, Clozapine, Ziprasidone and Olanzapine/Fluoxetine, and
- (iii) a pharmaceutically acceptable excipient, carrier or diluent.

16. A method of treating an Aβ-related pathology in a patient in need thereof, wherein said Aβ-related pathology is selected from the group consisting of β-amyloid angiopathy, Alzheimer's disease, attention deficit symptoms associated with Alzheimer's disease, and neurodegeneration associated with Alzheimer's disease, comprising administering to the patient a therapeutically effective amount of a compound according to claim 1, or a pharmaceutically acceptable salt thereof.

17. The method according to claim 16, wherein the Aβ-related pathology is Alzheimer's disease.

18. A method of treating an Aβ-related pathology in a patient in need thereof, wherein said Aβ-related pathology is selected from the group consisting of β-amyloid angiopathy, Alzheimer's disease, attention deficit symptoms associated with Alzheimer's disease, and neurodegeneration associated with Alzheimer's disease, comprising administering to the patient a therapeutically effective amount of a compound according to claim 1, or a pharmaceutically acceptable salt thereof, and at least one cognitive enhancing agent, memory enhancing agent, or acetyl cholinesterase inhibitor.

19. A method of treating an Aβ-related pathology in a patient in need thereof, wherein said Aβ-related pathology is selected from the group consisting of β-amyloid angiopathy, Alzheimer's disease, attention deficit symptoms associated with Alzheimer's disease, and neurodegeneration associated with Alzheimer's disease, comprising administering to the patient a therapeutically effective amount of a pharmaceutical composition comprising (i) a compound of formula (Ia) according to claim 8, or a pharmaceutically acceptable salt thereof, (ii) at least one agent selected from the group consisting of onepezil, galantamine, rivastigmine, tacrine and memantine Olanzapine, Aripiprazole, Risperidone, Quetiapine, Clozapine, Ziprasidone and Olanzapine/Fluoxetine.

* * * * *